United States Patent
Matsumura et al.

(10) Patent No.: US 7,582,148 B2
(45) Date of Patent: Sep. 1, 2009

(54) WOOD PRESERVATIVE COMPOSITION AND WOOD TREATMENT METHOD

(75) Inventors: Kazuyuki Matsumura, Annaka (JP); Akira Yamamoto, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 503 days.

(21) Appl. No.: 11/480,867

(22) Filed: Jul. 6, 2006

(65) Prior Publication Data

US 2007/0006771 A1    Jan. 11, 2007

(30) Foreign Application Priority Data

Jul. 8, 2005    (JP)    ............................. 2005-199531

(51) Int. Cl.
- *A01N 55/10* (2006.01)
- *A01N 25/00* (2006.01)
- *A01N 59/14* (2006.01)
- *B05D 1/18* (2006.01)
- *B27K 3/02* (2006.01)
- *B27K 3/34* (2006.01)
- *C07F 7/18* (2006.01)

(52) U.S. Cl. ................. 106/15.05; 106/18.3; 106/18.35; 427/297; 427/427.1; 427/428.01; 427/429; 427/440; 514/63; 556/401; 556/402; 556/439

(58) Field of Classification Search ............ 106/15.05, 106/18.3, 18.35; 427/297, 427.7, 428.01, 427/429, 440; 514/63; 556/401, 402, 439

See application file for complete search history.

(56) References Cited

U.S. PATENT DOCUMENTS

| | | | | |
|---|---|---|---|---|
| 5,441,667 | A | * | 8/1995 | Tonomura et al. ........... 510/159 |
| 6,372,231 | B1 | * | 4/2002 | Miura ........................ 424/401 |
| 2005/0228056 | A1 | * | 10/2005 | Asai et al. ..................... 516/53 |
| 2007/0006771 | A1 | * | 1/2007 | Matsumura et al. ........... 106/12 |

FOREIGN PATENT DOCUMENTS

| | | |
|---|---|---|
| JP | 8-197509 A | 8/1996 |
| JP | 8-198711 A | 8/1996 |
| JP | 10-7502 A | 1/1998 |
| JP | 2005194248 A * | 7/2005 |

OTHER PUBLICATIONS

"Wood Chemistry and Utilization Technolgy II, No. 2, the Japan Wood Society, pp. 21-38 (1991)".

* cited by examiner

*Primary Examiner*—Anthony J Green
(74) *Attorney, Agent, or Firm*—Birch, Stewart, Kolasch & Birch, LLP

(57) ABSTRACT

A wood preservative composition comprising an aqueous preservative and 0.001-1.0 wt % of a polyether-modified silicone having a specific structure is provided. The polyether-modified silicone reduces the surface tension of the composition and helps the preservative penetrate deeply into the wood interior.

7 Claims, No Drawings

WOOD PRESERVATIVE COMPOSITION AND WOOD TREATMENT METHOD

CROSS-REFERENCE TO RELATED APPLICATION

This non-provisional application claims priority under 35 U.S.C. §119(a) on Patent Application No. 2005-199531 filed in Japan on Jul. 8, 2005, the entire contents of which are hereby incorporated by reference.

TECHNICAL FIELD

This invention relates to wood preservative compositions, and more particularly, to wood preservative compositions comprising an aqueous preservative and a polyether-modified silicone, having an ability for the preservative to penetrate into wood to a depth. It also relates to a wood treatment method using the same.

BACKGROUND ART

For protecting wood from destroying organisms, it is well known to impregnate wood with preservatives. Typical impregnating techniques used include pressure impregnation, dipping, surface treatment and the like.

In order that these protective treatments be effective, the following two requirements must be met independent of a particular impregnation technique. The first requirement is that impregnated wood is fully toxic to wood destroying organisms such as wood boring beetles, termites and decay fungi. It is also required that the preservative penetrate into the wood interior. Most wood preservatives satisfy the first requirement, but few satisfy the second requirement. There are frequent accidents that impregnated wood is degraded from the interior where little of the preservative reaches. An improvement in this regard is desired.

The penetration of preservatives may be improved by dissolving the preservatives in organic solvents or by adding small amounts of surfactants to aqueous preservatives. The dissolution in organic solvents is noticeably effective due to the low surface tension of organic solvents, but undesirable because of the problems of environmental pollution and volatile organic compounds (VOC). The addition effect of ordinary surfactants is limited, with few exerting satisfactory effects.

Prior Art 1: Yuji Imamura, the Japan Wood Society researcher meeting report entitled "Wood Chemistry and Utilization Technology II," No. 2, the Japan Wood Society, pp. 21-38 (1991)

Prior Art 2: JP-A 08-197509
Prior Art 3: JP-A 08-198711
Prior Art 4: JP-A 10-007502

DISCLOSURE OF THE INVENTION

An object of the prevent invention is to provide a wood preservative composition having an improved ability for the preservative to penetrate into wood, and a wood treatment method using the same.

The inventor has discovered that the above and other objects can be attained using a specific polyether-modified silicone.

One embodiment of the invention provides a wood preservative composition comprising an aqueous preservative and a polyether-modified silicone having the general formula (1) and/or (2) in an amount of 0.001 to 1.0% by weight based on the total weight of the composition.

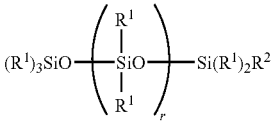

$R^1$ is each independently an alkyl, aryl, aralkyl or fluoroalkyl radical having 1 to 30 carbon atoms, $R^2$ is a polyoxyalkylene radical of the general formula (3):

$$-C_xH_{2x}O-(C_2H_4O)_y(C_3H_6O)_z-R^3 \quad (3)$$

wherein $R^3$ is hydrogen, a monovalent hydrocarbon radical of 1 to 30 carbon atoms, or an organic radical of the formula: $R^4-(CO)-$ wherein $R^4$ is a monovalent hydrocarbon radical of 1 to 10 carbon atoms, x is an integer of 2 to 5, y is an integer of 5 to 15, and z is an integer of 0 to 10, p is an integer of 0 to 3, q is an integer of 1 to 2, and r is an integer of 0 to 6.

In preferred embodiments, the aqueous preservative comprises a boron compound, and the polyether-modified silicone has the general formula (4).

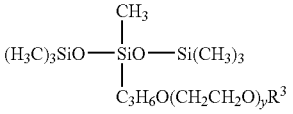

Herein $R^3$ is hydrogen, a monovalent hydrocarbon radical of 1 to 30 carbon atoms, or an organic radical of the formula: $R^4-(CO)-$, $R^4$ is a monovalent hydrocarbon radical of 1 to 10 carbon atoms, and y is an integer of 5 to 15. More preferably $R^3$ is hydrogen or methyl.

Another embodiment of the invention provides a wood treatment method comprising the step of treating wood with the wood preservative composition by surface treatment, dipping or pressure impregnation for causing the aqueous preservative to penetrate into the wood interior.

BENEFITS OF THE INVENTION

The wood preservative composition in which a polyether-modified silicone of specific structure is added to an aqueous preservative is successful in significantly enhancing the ability for the preservative to penetrate into wood.

DESCRIPTION OF THE PREFERRED EMBODIMENTS

The wood preservative composition according to one embodiment of the invention comprises an aqueous preservative and a polyether-modified silicone.

Any aqueous preservatives commonly used for wood may be used. Examples of suitable preservatives include, but are not limited to, chromium-copper-arsenic compounds (CCA), alkylammonium compounds (AAC), copper-chromium-zinc compounds (CFKZ), copper-boron-azole compounds (CUAZ), copper-alkylammonium compounds (ACQ), and boron compounds (e.g., boric acid and borates). Among these, aqueous preservatives comprising boron compounds are preferred because they are safe and environment friendly. Illustrative examples of boron compounds include boric acid, borax, borates ($Na_2B_8O_{13} \cdot 4H_2O$) commercially available as Tim-bor® from U.S. Borax Co., condensates of borate with ethylene glycol commercially available as Bora-Care® from Nisus Corp., and condensates of borate with propylene glycol commercially available as ProBor® from Safeguard Chemical.

The aqueous preservatives are typically dissolved in suitable solvents such as water and polyhydric alcohols (e.g., ethylene glycol) in a concentration of 0.01 to 50% by weight, preferably 0.1 to 20% by weight before they are ready for use. The solvent used herein is typically water or an aqueous solvent comprising water and a water-miscible polyhydric alcohol such as ethylene glycol in a concentration of 0 to 70% by weight.

The polyether-modified silicone used herein is selected from the general formulae (1) and (2).

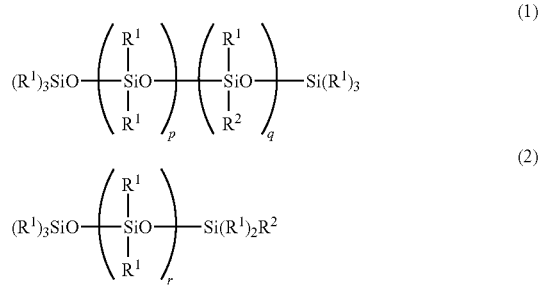

Herein $R^1$ which may be the same or different is an alkyl, aryl, aralkyl or fluoroalkyl radical having 1 to 30 carbon atoms. Examples include alkyl radicals such as methyl, ethyl, propyl, butyl, pentyl, hexyl, heptyl, octyl, nonyl and decyl; cycloalkyl radicals such as cyclopentyl and cyclohexyl; aryl radicals such as phenyl and tolyl; aralkyl radicals such as benzyl and phenethyl; and fluoroalkyl radicals such as trifluoropropyl and heptadecafluorodecyl. Preferred radicals of $R^1$ are those of 1 to 6 carbon atoms, for example, methyl, ethyl, propyl, butyl and phenyl. More preferably at least 80 mol % of entire $R^1$ are methyl.

$R^2$ is a polyoxyalkylene radical of the general formula (3):

$$—C_xH_{2x}O—(C_2H_4O)_y(C_3H_6O)_z—R^3 \quad (3)$$

wherein $R^3$ is hydrogen, a monovalent hydrocarbon radical of 1 to 30 carbon atoms, or an organic radical of the formula: $R^4—(CO)—$ wherein $R^4$ is a monovalent hydrocarbon radical of 1 to 10 carbon atoms.

The monovalent hydrocarbon radicals represented by $R^3$ include alkyl, alkenyl, aryl and other radicals, with the alkyl radicals being preferred. More preferred are those radicals of 1 to 6 carbon atoms, especially 1 to 3 carbon atoms. The monovalent hydrocarbon radicals represented by $R^4$ include alkyl, alkenyl, aryl and other radicals, with the alkyl radicals being preferred. More preferred are those radicals of 1 to 3 carbon atoms. Illustrative examples of $R^3$ include hydrogen, methyl, ethyl, propyl, butyl, and acetyl, with hydrogen and methyl being most preferred.

The subscript x is an integer of 2 to 5 ($2 \leq x \leq 5$), and y is an integer of 5 to 15 ($5 \leq y \leq 15$), preferably $7 \leq y \leq 12$. While the propylene oxide moiety facilitates handling of the polyether-modified silicone at low temperatures, z is 0 or an integer of equal to or less than 10 ($0 \leq z \leq 10$).

It is noted that if the polyoxyalkylene moiety in formula (3) is composed of both ethylene oxide units and propylene oxide units, the moiety may be either a block copolymer or a random copolymer of both the units.

In formula (1), the subscript p is an integer of 0 to 3, and q is an integer of 1 to 2. In formula (2), r is an integer of 0 to 6, preferably 0 to 3.

In a preferred embodiment, the polyether-modified silicone has the general formula (4):

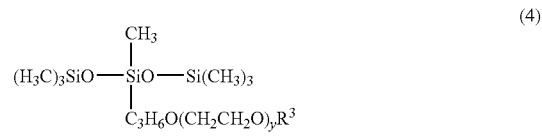

wherein $R^3$ and y are as defined above.

The polyether-modified silicones described above are commercially available, for example, as KF-643 from Shin-Etsu Chemical Co., Ltd. and Silwet L-77 from General Electric Co.

In the following description of compounds, symbols M and D are used as are common in the silicone art. As used herein, M designates $(H_3C)_3SiO_{1/2}$ units, D designates $(H_3C)_2SiO$ units, $M^H$ and $D^H$ designate units of M and D in which one of methyl radicals is hydrogen, respectively, and $M^R$ and $D^R$ designate units of M and D in which one of methyl radicals is substituted by substituent R, respectively. Beside, n-Bu stands for butyl.

The polyether-modified silicones of formula (1) or (2) may be prepared by addition reaction of organohydrogenpolysiloxanes and polyoxyalkylene compounds. Examples of the organohydrogenpolysiloxanes used as the starting reactant for the silicones of formula (1) include $M_2D^H$, $M_2DD^H$, $M_2D_2D^H$, $M_2D_3D^H$, $M_2DD^H{}_2$, $M_2D_2D^H{}_2$, and $M_2D_3D^H{}_2$, in isolated form or equilibrated mixture. Preferred are those of formula (1) wherein q=0 or 1, i.e., $M_2D^H$, $M_2DD^H$, $M_2D_2D^H$, and $M_2D_3D^H$. Most preferred are trisiloxanes $M_2D^H$.

Examples of the organohydrogenpolysiloxanes used as the starting reactant for the silicones of formula (2) include $MM^H$, $MDM^H$, $MD_3M^H$, and $M^{n-Bu}D_{4.5}M^H$. $MDM^H$ may be either an equilibrated mixture or a mixture of $M^{n-Bu}D_3M^H$ and $M^{n-Bu}D_6M^H$ like $M^{n-Bu}D_{4.5}M^H$. Preferred is $MM^H$ or $MD_3M^H$, with $MD_3M^H$ being most preferred.

The polyoxyalkylene compounds subject to addition reaction with the organohydrogenpolysiloxanes have the general formula (5):

$$C_xH_{2x-1}O—(C_2H_4O)_y(C_3H_6O)_z—R^3 \quad (5)$$

wherein $R^3$, x, y, and z are as defined in formula (3).

In the addition reaction, the organohydrogenpolysiloxane and the polyoxyalkylene compound are used in such amounts that the molar ratio of terminal unsaturated radicals to SiH radicals is from 0.8 to 1.5, preferably from 0.9 to 1.2.

The addition reaction is desirably performed in the presence of a platinum or rhodium catalyst. Suitable catalysts include chloroplatinic acid, alcohol-modified chloroplatinic acid, chloroplatinic acid-vinyl siloxane complexes and the like. Sodium acetate or sodium citrate may be added as a co-catalyst. The catalyst is used in a catalytic amount, preferably equal to or less than 50 ppm of platinum or rhodium, more preferably equal to or less than 20 ppm of platinum or rhodium.

If necessary, the addition reaction is performed in an organic solvent. Suitable organic solvents include aliphatic alcohols such as methanol, ethanol, 2-propanol and butanol; aromatic hydrocarbons such as toluene and xylene; aliphatic or alicyclic hydrocarbons such as n-pentane, n-hexane and cyclohexane; and halogenated hydrocarbons such as dichloromethane, chloroform and carbon tetrachloride. Although addition reaction conditions are not particularly limited, the reaction is preferably performed under reflux for about 1 to 10 hours.

In the wood preservative composition of the invention, the polyether-modified silicone is added in an amount of 0.001 to 1.0% by weight, preferably 0.05 to 0.5% by weight, based on the total weight of the composition prior to use. The polyether-modified silicone serves to reduce the surface tension of the aqueous preservative and at the same time, helps the preservative penetrate fast through wood tracheids and cinclides, increasing the penetrating ability of the preservative.

Other additives may be added to the wood preservative composition of the invention as long as they have no negative impact on the objects of the invention. For example, antifoaming agents, typically silicone antifoaming agents comprising silicone fluid and silica may be added for inhibiting the composition from foaming.

The wood preservative composition of the invention may be applied to wood by surface treatment using a roller, brush, spray or the like, or by dipping if desired. Also impregnation may be carried out under atmospheric pressure, reduced pressure or increased pressure. This is followed by drying while the drying technique may be by holding at room temperature, drying in daylight, or heat drying. The surface treatment, dipping or pressure impregnation may be carried out by the standard technique.

EXAMPLE

Examples of the invention are given below by way of illustration and not by way of limitation.

The polyether-modified silicones used have the average structural formulae shown below.

Polyether-Modified Silicone 1:

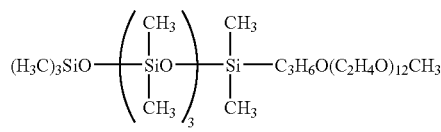

Polyether-Modified Silicone 2:

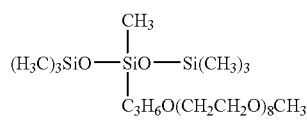

Aqueous Preservative 1:

It is a borate aqueous solution obtained by mixing a borate ($Na_2B_8O_{13} \cdot 4H_2O$, Tim-bor® by U.S. Borax) with deionized water for dissolution to a concentration of 15% by weight.

Aqueous Preservative 2:

A 500-ml four-necked flask equipped with a condenser, thermometer and ester adapter was charged with 100 g of a borate ($Na_2B_8O_{13} \cdot 4H_2O$, Tim-bor® by U.S. Borax), 50 g of glycerin, 180 g of ethylene glycol, and 20 g of water, and with stirring, heated to 150° C., at which reaction run while distilling off water. The reaction was continued for 1 hour until water was no longer distilled out. At the end of reaction, cooling yielded a pale yellow clear viscous liquid which was an ethylene glycol solution of glycerin-modified borate. The solution, which had a borate concentration of 30% by weight, was diluted with deionized water to a concentration of 20% by weight.

Wood 1:
Radiata pine wood as air dried; a rectangular block of 5×5 cm butt end size and 10 cm height was filled with an epoxy resin at both butt ends.

Wood 2:
White wood (Picea abies) as air dried; a rectangular block of 5×5 cm butt end size and 10 cm height was filled with an epoxy resin at both butt ends.

Wood 3:
Douglas fir wood as air dried; a rectangular block of 10×10 cm butt end size and 100 cm height was filled with an epoxy resin at both butt ends.

Wood 4:
Japanese larch wood as air dried; a rectangular block of 10×10 cm butt end size and 100 cm height was filled with an epoxy resin at both butt ends.

Examples 1-5 & Comparative Examples 1-6

Using the above-identified Polyether-modified silicones 1 and 2 and Aqueous preservatives 1 and 2, wood preservative compositions were prepared according to the formulation shown in Table 1. Each preservative composition was applied to surfaces of a wood block other than the butt ends by the following technique.

Application Technique 1:
The surfaces of a wood block other than the butt ends were brush coated with the preservative composition in a coating weight of 200 g/m², after which the block was aged under 25° C./55% RH conditions for 2 days.

Application Technique 2:
Using a reduced/increased pressure impregnation apparatus, a wood block was placed in the kettle and impregnated with the preservative composition under conditions: at room temperature and a reduced pressure of 0.08 MPa for 30 minutes and then at room temperature and an increased pressure of 1.0 MPa for 2 hours. After the impregnation, the block was aged under 25° C./55% RH conditions for 5 days.

Measuring the Depth of Penetration of the Preservative into Wood Interior

The wood block as aged was cut into halves in a height direction. The test involved spraying a solution of curcumin in ethanol to the newly cut butt end of the half block, drying, and spraying again a solution of dilute hydrochloric acid in salicylic acid whereupon the presence of borate turned the area red (curcumin color reaction). The penetration depth was measured as a distance from the outer surface (curly or straight grain surface) to the inside end of the red-tinted area.

The results are shown in Table 2.

TABLE 1

| | Aqueous preservative | | Polyether-modified silicone | | Other surfactant | | Surface tension (mN/m) |
|---|---|---|---|---|---|---|---|
| | Type | Amount (pbw) | Type | Amount (pbw) | Type | Amount (pbw) | |
| Example 1 | 1 | 100 | 1 | 0.1 | — | — | 23.6 |
| Example 2 | 1 | 100 | 2 | 0.1 | — | — | 23.0 |
| Example 3 | 1 | 100 | 2 | 0.5 | — | — | 22.0 |
| Example 4 | 2 | 100 | 1 | 0.1 | — | — | 22.9 |
| Example 5 | 2 | 100 | 2 | 0.1 | — | — | 22.0 |
| Comparative Example 1 | 1 | 100 | — | — | — | — | 72.8 |
| Comparative Example 2 | 2 | 100 | — | — | — | — | 57.0 |
| Comparative Example 3 | 1 | 100 | — | — | Na dodecylsulfate | 0.1 | 43.0 |
| Comparative Example 4 | 2 | 100 | — | — | Na dodecylsulfate | 0.1 | 42.9 |
| Comparative Example 5 | 1 | 100 | — | — | polyethylene glycol 200 | 1.0 | 52.0 |
| Comparative Example 6 | 2 | 100 | — | — | polyethylene glycol 200 | 1.0 | 51.0 |

TABLE 2

| | Wood | Application technique 1 Penetration depth (mm) | Wood | Application technique 2 Penetration depth (mm) |
|---|---|---|---|---|
| Example 1 | 1 | 10~11 | 3 | 20~25 |
| | 2 | 5~6 | 4 | 15~18 |
| Example 2 | 1 | 11~12 | 3 | 22~25 |
| | 2 | 6~7 | 4 | 18~20 |
| Example 3 | 1 | 12~13 | 3 | 22~25 |
| | 2 | 6~7 | 4 | 18~20 |
| Example 4 | 1 | 11~12 | 3 | 23~26 |
| | 2 | 7~8 | 4 | 19~20 |
| Example 5 | 1 | 13~15 | 3 | 24~27 |
| | 2 | 7~8 | 4 | 18~20 |
| Comparative Example 1 | 1 | 2~3 | 3 | 9~10 |
| | 2 | 1~2 | 4 | 5~6 |
| Comparative Example 2 | 1 | 3~5 | 3 | 14~16 |
| | 2 | 1~2 | 4 | 7~8 |
| Comparative Example 3 | 1 | 2~3 | 3 | 9~10 |
| | 2 | 1~2 | 4 | 5~6 |
| Comparative Example 4 | 1 | 3~4 | 3 | 13~15 |
| | 2 | 1~2 | 4 | 7~8 |
| Comparative Example 5 | 1 | 3~4 | 3 | 9~10 |
| | 2 | 1~2 | 4 | 5~6 |
| Comparative Example 6 | 1 | 3~4 | 3 | 14~15 |
| | 2 | 1~2 | 4 | 7~8 |

As is evident from Tables 1 and 2, the compositions of the invention have an extremely low surface tension as compared with the comparative compositions, proving that the polyether-modified silicones according to the invention help the preservatives penetrate deeply into the wood interior.

Japanese Patent Application No. 2005-199531 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A wood preservative composition comprising an aqueous preservative and 0.001 to 1.0% by weight based on the total weight of the composition of a polyether-modified silicone having the general formula (1) and/or (2):

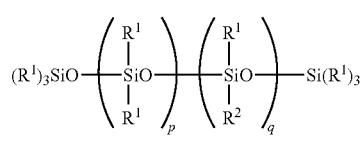

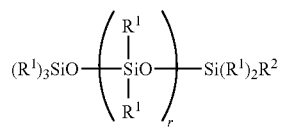

wherein $R^1$ is each independently an alkyl, aryl, aralkyl or fluoroalkyl radical having 1 to 30 carbon atoms, $R^2$ is a polyoxyalkylene radical of the general formula (3):

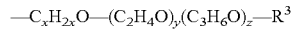

wherein $R^3$ is hydrogen, a monovalent hydrocarbon radical of 1 to 30 carbon atoms, or an organic radical of the formula: $R^4$—(CO)—, $R^4$ is a monovalent hydrocarbon radical of 1 to 10 carbon atoms, x is an integer of 2 to 5, y is an integer of 5 to 15, z is an integer of 0 to 10, p is an integer of 0 to 3, q is an integer of 1 to 2, and r is an integer of 0 to 6.

2. The wood preservative composition of claim 1 wherein said aqueous preservative comprises a boron compound.

3. The wood preservative composition of claim 1 wherein said polyether-modified silicone has the general formula (4):

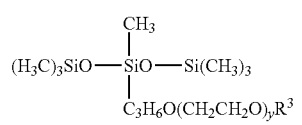

wherein $R^3$ is hydrogen, a monovalent hydrocarbon radical of 1 to 30 carbon atoms, or an organic radical of the formula: $R^4$—(CO)—, $R^4$ is a monovalent hydrocarbon radical of 1 to 10 carbon atoms, and y is an integer of 5 to 15.

4. The wood preservative composition of claim 3 wherein $R^3$ in formula (4) is hydrogen or methyl.

5. A wood treatment method comprising treating wood with the wood preservative composition of claim 1 by surface treatment, dipping or pressure impregnation for causing the aqueous preservative to penetrate into the wood.

6. The wood preservative composition of claim 4, wherein $R^3$ is methyl and y is 8.

7. A wood preservative composition comprising an aqueous preservative and 0.001 to 1.0% by weight based on the total weight of the composition of a polyether-modified silicone having the formula

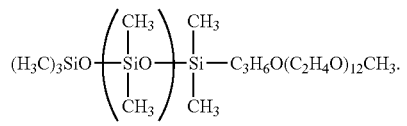

* * * * *